United States Patent [19]

Kumazawa et al.

[11] 4,277,632

[45] Jul. 7, 1981

[54] PROCESS FOR THE PRODUCTION OF ALKYLENE GLYCOLS

[75] Inventors: Toshihiko Kumazawa, Yokohama; Takeshi Yamamoto, Tokyo; Hiroshi Odanaka, Yokosuka, all of Japan

[73] Assignee: Nippon Shokubai Kaguku Kogyo Co., Ltd., Osaka, Japan

[21] Appl. No.: 76,842

[22] Filed: Sep. 19, 1979

[30] Foreign Application Priority Data

| Jul. 9, 1979  | [JP] | Japan | 54-85935 |
| Jul. 12, 1979 | [JP] | Japan | 54-87510 |
| Jul. 20, 1979 | [JP] | Japan | 54-91695 |
| Jul. 24, 1979 | [JP] | Japan | 54-93218 |
| Jul. 30, 1979 | [JP] | Japan | 54-96155 |
| Aug. 1, 1979  | [JP] | Japan | 54-97377 |
| Aug. 6, 1979  | [JP] | Japan | 54-99471 |

[51] Int. Cl.$^3$ .................. C07C 31/20; C07C 33/035; C07C 33/05; C07C 33/30

[52] U.S. Cl. .................. 568/867; 568/700; 568/811; 568/857

[58] Field of Search ................ 568/867, 811, 857, 700

[56] References Cited

U.S. PATENT DOCUMENTS

| 2,807,651 | 9/1957  | Britton et al. ................ 568/867 |
| 2,833,787 | 5/1958  | Carlson et al. ................ 568/867 |
| 3,629,343 | 12/1971 | Levin et al. ................... 568/867 |
| 3,933,923 | 1/1976  | Osberghaus et al. ........ 568/867 |
| 4,014,945 | 3/1977  | Zimmerschied et al. ..... 568/867 |

Primary Examiner—Joseph E. Evans
Attorney, Agent, or Firm—Omri M. Behr

[57] ABSTRACT

A process for the production of alkylene glycols, which comprises causing a corresponding alkylene oxide to react with water in the presence of a catalyst of at least one member selected from the group consisting of molybdenum and tungsten.

23 Claims, No Drawings

PROCESS FOR THE PRODUCTION OF ALKYLENE GLYCOLS

This invention relates to a process for the production of alkylene glycols, and more particularly it relates to a process for producing alkylene glycols involving a high percentage yield of a monoalkylene glycol by causing a corresponding alkylene oxide to react with water in the presence of a catalyst of at least one member selected from the group consisting of molybdenum and tungsten.

Alkylene glycols such as ethylene glycol and propylene glycol have heretofore been extensively used as raw materials for polyesters, polyethers, antifreezes, surfactants, etc.

Heretofore for the manufacture of alkylene glycols by the reaction of the corresponding alkylene oxides with water, a method which effects the reaction by use of a catalyst such as of sulfuric acid (U.S. Pat. No. 2,255,411) and a method which carries out the reaction at an elevated temperature and increased pressure without use of any catalyst have been adopted on commercial scales. In addition to forming monoalkylene glycols, however, these methods inevitably by-produce large amounts of dialkylene glycols, trialkylene glycols, tetraalkylene glycols and other polyalkylene glycols. Generally in the uses which are found for alkylene glycols, those for dialkylene glycols, trialkylene glycols, tetraalkylene glycols and other polyalkylene glycols are limited compared with those for monoalkylene glycols. In the production of alkylene glycols by the reaction of alkylene oxides with water, therefore, need is felt for the desirability of the development of a method which is capable of producing alkylene glycols having monoalkylene glycols formed therein in high percentages.

The proportions in which the various alkylene glycols are formed by the reaction of a corresponding alkylene oxide with water depend on the molar ratio of water to the alkylene oxide. To increase the proportion of monoalkylene glycol in the total composition of alkylene glycols formed by the reaction, it is necessary to increase the molar ratio of water to the alkylene oxide. Generally, the conversion of an alkylene oxide to corresponding alkylene glycols is effected by bringing to completion the reaction of the alkylene oxide with such a large excess of water as to give a water:alkylene oxide molar ratio in the range of from 10:1 to 20:1 under the conditions of 5 to 25 kg/cm$^2$G. of pressure and 100° to 200° C. of temperature in the presence or absence of a catalyst. The product which is obtained by the reaction of the alkylene oxide with the large excess of water, however, is a dilute aqueous solution containing alkylene glycols in a low concentration of from 5 to 30% by weight. To separate the alkylene glycols in a refined form from this dilute aqueous solution, removal of the large excess of water is inevitably entailed. This method, therefore, has the disadvantage that the removal of such excess water necessitate installation of a complicate apparatus such as an evaporator and huge consumption of energy.

Recently, in the production of alkylene glycols by the reaction of alkylene oxides with water, several methods have been proposed which are directed to reducing the molar ratio of water to the alkylene oxide to the order of 1 to 2.5 times the stoichiometric value and to increasing the proportion of monoalkylene glycol to the total composition of alkylene glycols produced. For example, British Pat. No. 1,177,877 discloses a method which causes the hydration of an alkylene oxide under the conditions of 10 to 80 atmospheres of pressure and 80° to 220° C. of temperature in the presence of carbon dioxide, with an alkali metal, a halide or a quaternary ammonium salt used as a catalyst, Japanese Patent Laid-open Publication No. 127010/1976 a method which produces alkylene glycols by causing a corresponding alkylene oxide to react with water and carbon dioxide in an organic base such as triethylamine or pyridine, and Japanese Patent Laid-open Publication No. 19905/1975 a method which effects the production of alkylene glycols by hydrating a corresponding alkylene oxide in the presence of carbon dioxide, with a quaternary phosphonium salt used as a catalyst. These methods, however, have much to be desired, for their effects are not quite satisfactory, the catalysts used therein have the possibility of entailing the problem of corrosion to the equipment used for the reactions and the alkylene glycols produced thereby are not fully satisfactory in quality.

It is, therefore, an object of this invention to provide a novel process for the production of alkylene glycols.

Another object of this invention is to provide a process for the production of alkylene glycols, which permits particularly monoalkylene glycol to be formed in high selectivity by a simple and economical procedure without appreciably by-producing polyalkylene glycols such as dialkylene glycol and trialkylene glycol.

Still another object of this invention is to provide reduction in the molar ratio of water to the alkylene oxide to the order of about 1 to 5 times the stoichiometric value and, consequently, reduction in the utility cost in the steps of separation and purification of alkylene glycols which follows the completion of the reaction.

The object described above have now been accomplished by this invention which resides in a process for producing alkylene glycols by causing a corresponding alkylene oxide to react with water in the presence of a catalyst of at least one member selected from the group consisting of molybdenum and tungsten.

The alkylene oxides which are usable for the process of this invention are chiefly the compounds represented by the general formula I:

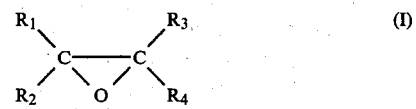

wherein, $R_1$, $R_2$, $R_3$ and $R_4$ each denote a hydrogen atom, an alkyl group having 1 to 3 carbon atoms, an aryl group having 6 carbon atoms, an alkenyl group having 2 or 3 carbon atoms or a cycloalkyl group having 3 to 6 carbon atoms. Typical of the compounds are ethylene oxide, propylene oxide, isobutylene oxide, 1,2-butylene oxide, 2,3-butylene oxide, pentylene oxide and styrene oxide. Of these typical compounds, preferable are ethylene oxide and propylene oxide. The most desirable alkylene oxide is ethylene oxide.

As the raw material for the reaction, there can be used any of the alkylene oxides which are obtained by all conceivable methods. In the case of ethylene oxide, for example, the ethylene oxide which is obtained by the method of catalytic oxidation, namely by causing ethylene to react with a molecular oxygen-containing gas such as air, oxygen-enriched air or pure oxygen in the gaseous phase in the presence of a catalyst containing mainly silver can be effectively used. Although it is particularly desirable to use ethylene oxide purified substantially to 100%, the ethylene oxide containing impurities which is obtained before the step of purification and the aqueous solution of ethylene oxide can be effectively used.

In consequence of the reaction, there is obtained an alkylene glycol of the general formula II:

wherein, $R_1$, $R_2$, $R_3$ and $R_4$ denote the same substituents as shown in the aforementioned general formula I, which corresponds to the alkylene oxide used in the reaction. Typical of the alkylene glycols thus produced are ethylene glycol, 1,2-propylene glycol, isobutylene glycol, 1,2-butylene glycol, 2,3-butylene glycol, pentylene glycol and styrene glycol.

Water of any kind can effectively used as the raw material in the reaction of this invention. Particularly, fresh water, the water demineralized by an ion-exchange treatment, the condensate of steam, the condensate issuing from the step of dehydration involved in the equipment for the production of alkylene oxide or alkylene glycol, etc. can be advantageously used. The amount of water to be used can be selected from the range of 1 to 30 mols, more commonly from 1 to 20 mols, per mol of the alkylene oxide. When the reaction of the alkylene oxide with water is carried out in the presence of carbon dioxide as will be touched upon afterward, or when the reaction which is carried out in the presence of nitrogen, air, etc. in place of carbon dioxide requires the reaction mixture to be adjusted to a pH value in the range of 5 to 10, the amount of water may be decreased to 1 to 5 mols per mol of the alkylene oxide. Although the amount of water may be further decreased depending on the type of reaction, it is desired to be slightly in excess of the stoichiometric amount, namely 1.01 to 5 mols per mol of the alkylene oxide.

As the catalyst for the process of this invention, molybdenum or tungsten is used in the form of pure metal or a compound. In the case of metallic molybdenum, it is desired to have a large surface area. For actual use as the catalyst, it may be prepared in the form of powder, grains like those of sand, granules, a metal gauze, a honeycomb or a sponge and, in that form, mixed, suspended or deposited as a fixed bed in the liquid phase of the reactants. Otherwise, the material of which the reactor is made may contain metallic molybdenum to serve as the catalyst. From the various forms described above, a suitable form may be selected in due consideration of such factors as the reactivity, ease of handling and cost. It is particularly desirable to use metallic molybdenum of a form which can be dispersed into very fine particles in the reaction system.

Molybdenum compounds which are suitable for use as the catalyst in the reaction include both inorganic and organic compounds such as, for example, oxides, sulfides, acids, halides, phosphorus compounds, poly acids, alkali metal salts of such acids and poly acids, alkaline earth metal salts of such acids and poly acids, ammonium salts of such acids and poly acids, heavy metal salts of acids and organic acids salts. Typical of these compounds are molybdenum dioxide, molybdenum trioxide, molybdenum disulfide, molybdic acid, molybdenum trichloride, molybdenum pentachloride, molybdenum tribromide, phosphomolybdic acid, ammonium phosphomolybdate, sodium molybdate, sodium paramolybdate, potassium molybdate, potassium paramolybdate, lithium molybdate, calcium molybdate, barium molybdate, ammonium molybdate, ammonium paramolybdate, iron molybdate and lead molybdate.

The metallic molybdenum and any of the molybdenum compounds described above may be used in the form of a mixture. Of the various molybdenum compounds which are usable as the catalyst for the reaction, particularly desirable are molybdic acid and salts thereof, especially alkali metal salts of molybdic acid such as sodium molybdate and potassium molybdate.

Where metallic tungsten is selected for use as the catalyst, it is desired to have a large surface area. For actual use, the metallic tungsten may be prepared in the form of powder, grains like those of sand, granules, a metal gauze, a honeycomb or a sponge and, in that form, mixed, suspended or deposited as a fixed bed in the liquid phase of the reactants. Otherwise, the material of which the reactor is made may contain metallic tungsten to serve as the catalyst. Of the various forms described above, a suitable form may be selected in due consideration of such factors as the reactivity, ease of handling and cost. It is particularly desirable to use metallic tungsten of a form which can be dispersed into very fine particles in the reaction system.

Tungsten compounds which are suitable for use as the catalyst in the reaction include both inorganic and organic compounds such as, for example, oxides, acids, halides, phosphorus compounds, poly acids, alkali metal as salts of such acids and poly acids, alkaline earth metal salts of such acids and poly acids, ammonium salts of such acids and poly acids, heavy metal salts of acids and organic acid salts. Typical of these compounds are tungsten dioxide, tungsten trioxide, tungstic acid, tungsten dichloride, tungsten pentachloride, tungsten dibromide, tungsten pentabromide, phosphotungstic acid, potassium tungstate, sodium tungstate, lithium tungstate, potassium paratungstate, sodium paratungstate, sodium metatungstate, calcium tungstate, barium tungstate, magnesium tungstate, ammonium tungstate, ammonium paratungstate, cadmium tungstate, cobalt tungstate, ferric tungstate, lead tungstate, cupric tungstate and bismuth tungstate.

The metallic tungsten and any of tungsten compounds described above may be used in the form of a mixture. Of the various tungsten compounds which are usable as the catalyst for the reaction, particularly desirable are tungstic acid and salts thereof, especially alkali metal salts of tungstic acid such as sodium tungstate and potassium tungstate.

The catalyst of at least one member selected from the group consisting of molybdenum and tungsten which is used in the reaction of the present invention is present in the reaction system in an amount of not less than 0.01% by weight, desirably in the range of from 0.1 to 100% by weight, preferably from 1 to 20% by weight, and most preferably from 2 to 15% by weight, based on the alkylene oxide.

The catalyst is used in its unmodified form, in a suitably molded form or in a form supported by the known method on a carrier such as of silica, alumina or zeolite. For actual use, the catalyst of such a form is dissolved, mixed, suspended or deposited as a fixed bed in the liquid phase of the reactants. The addition of the catalyst to the reactants may be effected by having the catalyst mixed in advance with the water used for the hydration or by means of an inlet separately installed in the reaction equipment. In any event, the catalyst is added in its whole amount at the beginning of the reaction or it is continuously or intermittently added at a fixed feed rate through the entire period of the reaction. A suitable manner of addition may be selected in due consideration of such factors as the type of reaction, the method of operation, etc.

The hydration of the alkylene oxide according to the present invention can be effectively carried out in the presence of an inert gas such as air, carbon dioxide or nitrogen, preferably in the presence of carbon dioxide and nitrogen and most preferably in the presence of carbon dioxide alone. Where the hydration of the alkylene oxide is carried out in the presence of carbon dioxide, the carbon dioxide is used in an amount falling in the range of from 0.00001 to 1 mol, preferably from 0.0001 to 1 mol, per mol of the alkylene oxide, under the reaction conditions of the present invention.

The carbon dioxide is generally added in a gaseous form. Otherwise, it may be added in the form of a compound which liberates carbon dioxide under the reaction conditions of this invention. Examples of compounds which are usable for this purpose are carbonates and bicarbonates of alkali metals. Typical of these compounds are sodium carbonate, potassium carbonate, lithium carbonate, sodium bicarbonate and potassium bicarbonate. Such a compound as the source of carbon dioxide can be added to the reactants without impairing the objects of this invention in any way. When the hydration of the alkalene oxide is carried out in the presence of carbon dioxide, the amount of water to be used in the reaction can be decreased to the order of 1 to 5 mols, preferably 1.01 to 5 mols, per mol of the alkylene oxide.

In the process of the present invention, the pH value of the reactant solution need not be specifically limited but may be varied in a wide range such as from 2 to 12. Better results of the reaction are obtained when the pH value is limited to the range of from 5 to 10, desirably from 6 to 8. The hydration of the alkylene oxide produces the best results when it is carried out with the pH value kept in the neutral point of about 7. In this case, the hydration can be performed in the presence of air, carbon dioxide or nitrogen.

Any acidic or alkaline substance can be used as an agent for keeping the pH value of the reaction solution in the range of from 5 to 10. Acidic substances include inorganic acids and organic acids. Typical of such acidic substances are molybdic acid, tungstic acid, sulfuric acid, hydrochloric acid, phosphoric acid and acetic acid. Alkaline substances include hydroxides, carbonates and bicarbonates of alkali metals, alcoholates and ammonium ion. Typical of such alkaline substances are sodium hydroxide, potassium hydroxide, sodium carbonate, potassium carbonate, sodium dicarbonate, potassium dicarbonate, ammonia and ammonium hydroxide. As regards the method of addition of the pH adjusting agent to the reaction solution, the solution of the catalyst and water may be adjusted to pH 5 to 10 by the addition of pH adjusting agent, or the reactant solution formed of the reactants and the catalyst may be adjusted to pH 5 to 10 by the addition of the pH adjusting agent or the reactant solution before or after the addition thereto of water may be adjusted to pH 5 to 10 by the addition of the pH adjusting agent. When the hydration of the alkylene oxide is carried out with the pH value of the reactant solution adjusted in the range of 5 to 10, the amount of water to be used in the reaction can be decreased to the order of 1 to 5 mols, preferably 1.01 to 5 mols, per mol of the alkylene oxide. In this case, the reaction produces the monoalkylene glycol with high selectivity. Particularly when the reaction is carried out in the presence of carbon dioxide with the pH value adjusted in the range of 5 to 10, the selectivity with which the monoalkylene glycol is produced is further improved. The pH adjustment coupled with the presence of carbon dioxide gives this conspicuous effect.

The reaction temperature, though variable with the kind of the catalyst, the initial composition of the reaction solution, etc., is generally in the range of from 20° to 240°, preferably, from 50° to 200° C. and most preferably from 80° to 200° C. The reaction pressure is maintained in the range of from 0 to 30 kg/cm$^2$G., preferably from 2 to 25 kg/cm$^2$G. so as to keep the alkylene oxide in the liquid phase. As occasion demands, the pressure inside the reactor may be suitably adjusted. The reaction in the present invention may be carried out batchwise, semi-batchwise or continuously.

As described above, the present invention represses the by-production of dialkylene glycol, trialkylene glycol and other polyalkylene glycols and permits the production of monoalkylene glycol with high selectivity by a process which comprises causing a corresponding alkylene oxide to react with water in the presence of a catalyst of at least one member selected from the group consisting of molybdenum and tungsten.

Now the process of this invention will be specifically described below by reference to working examples of the invention, which are cited solely for the purpose of illustration and are not meant to limit the present invention in any sense. Needless to mention, they admit of various modifications thereto without departing from the spirit of this invention.

As indicated in the examples which follow, the "conversion of alkylene oxide" and the "selectivity to monoalkylene glycol, dialkylene glycol and trialkylene glycol and others" represet the values calculated in accordance with the following formulas.

$$\text{Conversion of alkylene oxide (\%)} = \frac{\text{(Amount, in mol, of alkylene oxide before reaction)} - \text{(Amount, in mol, of alkylene oxide after reaction)}}{\text{Amount, in mol, of alkylene oxide before reaction}} \times 100$$

$$\text{Selectivity to monoalkylene glycol (\%)} = \frac{\text{Amount, in mol, of formed monoalkylene glycol}}{\text{Amount, in mol, of alkylene oxide reacted}} \times 100$$

$$\text{Selectivity to dialkylene glycol (\%)} = \frac{\text{(Amount, in mol, of formed dialkylene glycol)} \times 2}{\text{Amount, in mol, of alkylene oxide reacted}} \times 100$$

$$\text{Selectivity to trialkylene glycol and others (\%)} = \frac{\text{(Amount, in mol, of trialkylene glycol)} \times 3}{\text{Amount, in mol, of alkylene oxide reacted}} \times 100$$

EXAMPLE 1

A stainless steel autoclave having an inner volume of 500 ml and equipped with a stirrer was charged with 40 g of ethylene oxide, 300 g of water and 2 g of powdered metallic molybdenum as the catalyst which had been passed through a 200-mesh sieve. Then, the autoclave was sealed after nitrogen gas was introduced therein until the inner pressure thereof rose to 10 kg/cm$^2$G. The autoclave was submerged in an oil bath kept at 160° and left to stand therein for 120 minutes to allow the contents to react. Consequently, the ethylene oxide was completedly converted to ethylene glycols. On analysis of the formed ethylene glycols, the selectivity of the ethylene oxide as the raw material to monoethylene glycol, diethylene glycol and triethylene glycol and others was as shown in Table 1.

EXAMPLES 2-9

The procedure of EXAMPLE 1 was repeated, except that varying catalysts were used in varying amounts as indicated in Table 1. Consequently, the ethylene oxide used in each of EXAMPLES 2-9 was completely converted to ethylene glycols. On analysis of the formed ethylene glycols, the selectivity of the ethylene oxide as the raw material to monoethylene glycol, diethylene glycol and triethylene glycol and others was as shown in Table 1.

CONTROL 1

The procedure of EXAMPLE 1 was repeated, except that the use of the catalyst was omitted. Consequently, the ethylene oxide was completely converted to ethylene glycols. On analysis of the formed ethylene glycols, the selectivity of the ethylene oxide as the raw material to monoethylene glycol, diethylene glycol and triethylene glycol and others was as shown in Table 1.

In the tables given hereinafter, MEG, DEG and TEG stand for monoethylene glycol, diethylene glycol and triethylene glycol and others respectively.

TABLE 1

| Example | Catalyst | Amount added (g) | MEG (mol%) | DEG (mol%) | TEG (mol%) |
|---|---|---|---|---|---|
| 1 | Metallic molybdenum | 2 | 89.4 | 9.7 | 0.9 |
| 2 | Molybdenum disulfide | 2 | 88.8 | 10.1 | 1.1 |
| 3 | Molybdenum trioxide | 2 | 89.4 | 9.5 | 1.1 |
| 4 | Molybdic acid | 2 | 88.9 | 10.1 | 1.0 |
| 5 | Ammonium molybdate | 2 | 88.9 | 10.0 | 1.1 |
| 6 | Sodium molybdate | 2 | 91.5 | 7.6 | 0.9 |
| 7 | Potassium molybdate | 2 | 91.8 | 7.4 | 0.8 |
| 8 | Potassium molybdate | 4 | 93.7 | 5.7 | 0.6 |
| 9 | Potassium molybdate | 8 | 94.8 | 4.7 | 0.5 |
| Control 1 | None | 0 | 85.8 | 12.7 | 1.5 |

EXAMPLE 10

The procedure of EXAMPLE 1 was repeated, except that 150 g of ethylene oxide, 150 g of water and 7.5 g of potassium molybdate as the catalyst were used instead. Consequently, the ethylene oxide was completely converted to ethylene glycols. On analysis of the formed ethylene glycols, the selectivity of the ethylene oxide as the raw material to monoethylene glycol, diethylene glycol and triethylene glycol and others was as shown in Table 2.

CONTROL 2

The procedure of EXAMPLE 10 was repeated, except that the use of the catalyst was omitted. On analysis of formed ethylene glycols, the selectivity of the ethylene oxide as the raw material to monoethylene glycol, diethylene glycol and triethylene glycol and others was as shown in Table 2.

TABLE 2

| Example | Catalyst | Amount added (g) | MEG (mol%) | DEG (mol%) | TEG,etc. (mol%) |
|---|---|---|---|---|---|
| Example 10 | Potassium molybdate | 7.5 | 77.4 | 21.1 | 1.5 |
| Control 2 | Noen | 0 | 47.4 | 38.9 | 13.7 |

EXAMPLE 11

A stainless steel autoclave having an inner volume of 500 ml and equipped with a stirrer was charged with 50 g of ethylene oxide, 102 g of water and 2.5 g of potassium molybdate as the catalyst. Then, the autoclave was sealed after carbon dioxide gas was introduced therein until the inner pressure thereof rose to 10 kg/cm$^2$G. The autoclave was submerged in an oil bath kept at 160° C. and left to stand therein for two hours to allow the contents to react. Consequently, the ethylene oxide was completely converted to ethylene glycols. On analysis of the formed ethylene glycols, the selectivity of the ethylene oxide as the raw material to monoethylene glycol, diethylene glycol and trietylene glycol and others was found to be 85.9 mol% for monoethylene glycol, 13.5 mol% for diethylene glycol and 0.6 mol% for triethylene glycol and others.

EXAMPLE 12

The procedure of EXAMPLE 1 was repeated, except that 2 g of powdered metallic tungsten which had been passed through a 200-mesh sieve was used as the catalyst in place of metallic molybdenum. Consequently, the ethylene oxide was completely converted to ethylene glycols. On analysis of the formed ethylene glycols, the selectivity of the ethylene oxide as the raw material to monoethylene glycol, diethylene glycol and triethylene glycol and others was as shown in Table 3.

EXAMPLES 13-15

The procedure of EXAMPLE 1 was repeated, except that varying catalysts were used in varying amounts as indicated in Table 3. Consequently, the ethylene oxide used in each of EXAMPLES 13-15 was completely converted to ethylene glycols. On analysis of the formed ethylene glycols, the selectivity of the ethylene oxide as the raw material to monoethylene glycol, diethylene glycol and triethylene glycol and others was as shown in Table 3.

TABLE 3

| Example | Catalyst | Amount added (g) | MEG (mol%) | DEG (mol%) | TEG,etc. (mol%) |
|---|---|---|---|---|---|
| 12 | Metallic | 2 | 88.9 | 10.0 | 1.1 |

TABLE 3-continued

| Example | Catalyst | Amount added (g) | Selectivity | | |
|---|---|---|---|---|---|
| | | | MEG (mol%) | DEG (mol%) | TEG,etc. (mol%) |
| 13 | Sodium tungstate | 2 | 89.2 | 9.8 | 1.0 |
| 14 | Sodium tungstate | 4 | 91.7 | 7.4 | 0.9 |
| 15 | Sodium tungstate | 8 | 93.1 | 6.1 | 0.8 |

EXAMPLE 16

The procedure of EXAMPLE 11 was repeated, except that 2.5 g of sodium tungstate was used in place of potassium molybdenum. Consequently, the ethylene oxide was completely converted to ethylene glycols. On analysis of the formed ethylene glycols, the selectivity of the ethylene oxide as the raw material to monoethylene glycol, diethylene glycol and triethylene glycol and others was found to be 75.9 mol% for monoethylene glycol, 22.4 mol% for diethylene glycol and 1.7 mol% for triethylene glycol and others.

CONTROL 3

The procedure of EXAMPLE 16 was repeated, except that the use of the catalyst was omitted. Consequently, the ethylene oxide was completely converted to ethylene glycols. On analysis of the formed ethylene glycols, the selectivity of the ethylene oxide as the raw material to monoethylene glycol, diethylene glycol and triethylene glycol and others was found to be 56.8 mol% for monoethylene glycol, 31.6 mol% for diethylene glycol, 6.9 mol% for triethylene glycol and 4.7 mol% for tetraethylene glycol and other polyethylene glycols.

EXAMPLE 17

A stainless steel autoclave having an inner volume of 200 ml and equipped with a stirrer was charged with 1.6 g of potassium molybdate and 14.9 g of water and thereafter sealed. Then, the air entrapped inside the autoclave was thoroughly displaced with nitrogen gas. Subsequently, carbon dioxide gas was introduced into the autoclave until the inner pressure thereof rose to 1.3 kg/cm$^2$ G, 33.0 g of ethylene oxide was added thereto and nitrogen gas was forced in to bring the total inner pressure to 6 kg/cm$^2$ G. The autoclave thus filled was submerged in an oil bath kept at 140° C. and left to stand therein for 60 minutes to allow the contents to react. The inner pressure increased to 22.5 kg/cm$^2$ G after 21 minutes of the standing and thereafter fell to 7.7 kg/cm$^2$ G after 45 minutes of the standing. During the remaining period of the reaction time, the inner pressure was substantially unchanged.

The autoclave was cooled in an ice bath and, thereafter, the reaction solution was removed from the autoclave. On analysis, the reaction solution was found to contain less than 0.01% by weight of unaltered ethylene oxide, indicating that the conversion of ethylene oxide was substantially 100%. When the formed ethylene glycols were analyzed for percentage composition by gas chromatography, the selectivity of the ethylene oxide as the raw material to monoethylene glycol, diethylene glycol and triethylene glycol and others was found to be 88.2 mol%, 11.5 mol% and 0.3 mol% respectively.

EXAMPLE 18

The procedure of EXAMPLE 17 was repeated, except that the catalyst was changed to sodium molybdate. Consequently, the results of the reaction were as shown in Table 4.

EXAMPLES 19-20

The procedure of EXAMPLE 17 was repeated, except that the same catalyst was added in different amounts as indicated in Table 4. The results of the reaction were as shown in Table 4.

EXAMPLE 21-23

The procedure of EXAMPLE 17 was repeated, except that the amount of carbon dioxide gas was changed as indicated in Table 4 and the reaction was carried out at 120° C. for 90 minutes. The results of the reaction were as shown in Table 4.

EXAMPLES 24-25

The procedure of EXAMPLE 17 was repeated, except that the amount of water added was changed as indicated in Table 4. The results of the reaction were as shown in Table 4.

EXAMPLE 26

The procedure of EXAMPLE 17 was repeated, except that molybdic acid was used as the catalyst and potassium bicarbonate was used in place of carbon dioxide gas. The results of the reaction were as shown in Table 4.

CONTROL 4

The procedure of EXAMPLE 17 was repeated, except that the use of the catalyst was omitted and the reaction time was changed to 150 minutes. The results of the reaction were as shown in Table 4.

EXAMPLE 27

The procedure of EXAMPLE 17 was repeated, except that 1.6 g of sodium tungstate was used in place of potassium molybdate. In the course of the reaction, the inner pressure of the autoclave rose to 22.8 kg/cm$^2$ G after 27 minutes of the standing, then fell to 7.7 kg/cm$^2$ G after 45 minutes of the standing and remained substantially unchanged for the remaining period of the reaction time.

The autoclave was cooled in an ice bath and, thereafter, the reaction solution was removed from the autoclave. On analysis, the reaction solution was found to contain less than 0.01% by weight of unaltered ethylene oxide, indicating that the conversion of ethylene oxide was substantially 100%. When the formed ethylene glycols were analyzed for percentage composition by gas chromatography, the selectivity of the ethylene oxide as the raw material to monoethylene glycol, diethylene glycol and triethylene glycol and others was found to be 72.6 mol%, 25.0 mol% and 2.4 mol% respectively.

EXAMPLE 28

The procedure of EXAMPLE 27 was repeated, except that the catalyst was changed to potassium tungstate. The results of the reaction were as shown in Table 4.

EXAMPLE 29-30

The procedure of EXAMPLE 27 was repeated, except that the amount of the catalyst added was changed to the varying weights indicated in Table 4. The results of the reaction were as shown in Table 4.

EXAMPLE 31-33

The procedure of EXAMPLE 27 was repeated, except that the amount of the carbon dioxide gas added was changed to the varying amounts indicated in Table 4. The results of the reaction were as shown in Table 4.

EXAMPLES 34-35

The procedure of EXAMPLE 27 was repeated, except that the amount of water added was changed to the varying weights indicated in Table 4. The results of the reaction were as shown in Table 4.

EXAMPLES 36

The procedure of EXAMPLE 27 was repeated, except that the catalyst was changed to tungstic acid and the carbon dioxide gas was changed to potassium bicarbonate. The results of the reaction were as shown in Table 4.

EXAMPLE 37

A stainless steel autoclave having an inner volume of 200 ml and equipped with a stirrer was charged with 2.0 g of potassium molybdate, 21.6 g of water and 34.8 g of propylene oxide. Then, carbon dioxide gas supplied from a cylinder was introduced into the autoclave until the inner pressure thereof rose to 1.7 kg/cm$^2$ G. Then, the inner pressure of the autoclave was raised to 6 kg/cm$^2$ G by introduction of nitogen gas. The autoclave was sealed and submerged in an oil bath kept at 140° C. and left to stand therein for 120 minutes to allow the contents to react. In the course of the reaction, the inner pressure of the autoclave rose to 14.2 kg/cm$^2$ G. after 48 minutes of the standing and, thereafter, fell to 7.9 kg/cm$^2$ G. after 80 minutes of the standing and remained substantially unchanged for the remaining period of the reaction time.

The autoclave was cooled in an ice bath and, thereafter, the reaction solution was removed from the autoclave. On analysis, this reaction solution was found to contain less than 0.01% by weight of unaltered propylene oxide, indicating that the conversion of the propylene oxide was substantially 100%. The selectively of the propylene oxide as the raw material to monopropylene glycol, dipropylene glycol and polypropylene glycol and others was found to be 90.6 mol%, 8.8 mol% and 0.6 mol% respectively.

EXAMPLE 38

The procedure of EXAMPLE 37 was repeated, except that the catalyst was changed to sodium molybdate. The results of the reaction were as shown in Table 5.

EXAMPLE 39

The procedure of EXAMPLE 37 was repeated, except that the amount of the catalyst added was changed to the amount indicated in Table 5. The results of the reaction were as shown in Table 5.

TABLE 4

| | Raw material | | | Catalyst | | Reaction condition | | | Conversion | Selectivity | | |
|---|---|---|---|---|---|---|---|---|---|---|---|---|
| Example | EO (g) | Water (g) | CO$_2$ (mole) | Kind | to EO (wt.%) | Temp. (°C.) | Pressure (kg/cm$^2$G) | Time (min) | of EO (mol%) | MEG (mol%) | DEG (mol%) | TEC.etc. (mol%) |
| 17 | 33.0 | 14.9 | 0.01 | PM | 4.8 | 140 | 6 | 60 | 100 | 88.2 | 11.5 | 0.3 |
| 18 | 33.0 | 14.9 | 0.01 | SM | 4.8 | 140 | 6 | 60 | 100 | 87.5 | 12.1 | 0.4 |
| 19 | 33.0 | 14.9 | 0.02 | PM | 9.6 | 140 | 6 | 60 | 100 | 89.6 | 10.1 | 0.3 |
| 20 | 33.0 | 14.9 | 0.005 | PM | 2.4 | 140 | 6 | 60 | 100 | 81.4 | 17.4 | 1.2 |
| 21 | 33.0 | 14.9 | 0.001 | PM | 4.8 | 120 | 6 | 90 | 100 | 80.9 | 17.8 | 1.3 |
| 22 | 33.0 | 14.9 | 0.015 | PM | 4.8 | 120 | 6 | 90 | 100 | 84.9 | 14.5 | 0.6 |
| 23 | 33.0 | 14.9 | 0.08 | PM | 4.8 | 120 | 6 | 90 | 100 | 80.6 | 18.0 | 1.4 |
| 24 | 33.0 | 67.5 | 0.01 | PM | 4.8 | 140 | 6 | 60 | 100 | 92.1 | 7.6 | 0.3 |
| 25 | 33.0 | 27.0 | 0.06 | PM | 4.8 | 140 | 6 | 60 | 100 | 88.0 | 11.7 | 0.3 |
| 26 | 33.0 | 14.9 | KHCO$_3$ | MA | 3.3 | 140 | 6 | 60 | 100 | 80.5 | 18.2 | 1.3 |
| 27 | 33.0 | 14.9 | 0.01 | ST | 4.8 | 140 | 6 | 60 | 100 | 72.6 | 25.0 | 2.4 |
| 28 | 33.0 | 14.9 | 0.01 | PT | 4.8 | 140 | 6 | 60 | 100 | 67.0 | 28.1 | 4.9 |
| 29 | 33.0 | 14.9 | 0.02 | ST | 9.6 | 140 | 6 | 60 | 100 | 81.4 | 17.3 | 1.3 |
| 30 | 33.0 | 14.9 | 0.005 | ST | 2.4 | 140 | 6 | 60 | 100 | 66.2 | 28.6 | 5.2 |
| 31 | 33.0 | 14.9 | 0.001 | ST | 4.8 | 140 | 6 | 60 | 100 | 70.7 | 26.1 | 3.2 |
| 32 | 33.0 | 14.9 | 0.02 | ST | 4.8 | 140 | 6 | 60 | 100 | 71.5 | 25.7 | 2.8 |
| 33 | 33.0 | 14.9 | 0.08 | ST | 4.8 | 140 | 6 | 60 | 100 | 70.1 | 26.4 | 3.5 |
| 34 | 33.0 | 67.5 | 0.01 | ST | 4.8 | 140 | 6 | 60 | 100 | 83.3 | 15.7 | 1.0 |
| 35 | 33.0 | 27.0 | 0.01 | ST | 4.8 | 140 | 6 | 60 | 100 | 78.5 | 19.8 | 1.7 |
| 36 | 33.0 | 14.9 | KHCO$_3$ | TA | 3.3 | 140 | 6 | 60 | 100 | 70.5 | 26.2 | 3.3 |
| Control 4 | 33.0 | 14.9 | 0.01 | — | — | 140 | 6 | 150 | 100 | 36.1 | 32.9 | 31.0 |

EO: ethlyene oxide, PM: potassium molybdate, SM: sodium molybdate, MA: molybdic acid, ST: sodium tungstate, PT: potassium tungstate, TA: tungstic acid

EXAMPLE 40-41

The procedure of EXAMPLE 37 was repeated, except that the amount of the carbon dioxide was changed as indicated in Table 5. The results of the reaction were as shown in Table 5.

EXAMPLES 42-43

The procedure of EXAMPLE 37 was repeated, except that the amount of water as the raw material for the reaction was changed as indicated in Table 5. The results of the reaction were as shown in Table 5.

EXAMPLE 44

The procedure of EXAMPLE 37 was repeated, except that the catalyst was changed to 1.7 g of molybdic acid and the carbon dioxide gas was changed to potassium bicarbonate. The results of the reaction were as shown in Table 5.

EXAMPLE 45

The procedure of EXAMPLE 37 was repeated, except that the propylene oxide as the raw material was changed to 43.3 g of 1,2-butylene oxide and the reaction time was changed to 240 minutes. The results of the reaction shown in Table 6 indicate that the conversion of 1,2-butylene oxide was substantially 100% and the selectivity of the raw material to monobutylene glycol was 93.7%.

CONTROL 5

The procedure of EXAMPLE 37 was repeated, except that the addition of the catalyst was omitted and the reaction time was changed to 240 minutes. The results of the reaction were as shown in Table 5.

EXAMPLE 46

The procedure of EXAMPLE 37 was repeated, except that 2.0 g of sodium tungstate was used in place of potassium molybdate. In the course of the reaction, the inner pressure of the autoclave rose to 16.3 kg/cm$^2$ G. after 45 minutes of the standing, fell to 8.0 kg/cm$^2$ G. after 100 minutes of the standing and, thereafter, remained substantially unchanged for the remaining period of the reaction time.

The autoclave was cooled in an ice bath and the reaction solution was removed. On analysis, this reaction solution was found to contain less than 0.01% by weight of unaltered propylene oxide, indicating that the conversion of the propylene oxide was substantially 100%. The selectivity of the propylene oxide as the raw material to monopropylene glycol, dipropylene glycol and tripropylene glycol and others was found to be 80.4 mol%, 18.6 mol% and 1.0 mol% respectively.

EXAMPLE 47

The procedure of EXAMPLE 46 was repeated, except that the catalyst was changed to potassium tungstate. The results of the reaction was as shown in Table 5.

EXAMPLE 48

The procedure of EXAMPLE 46 was repeated, except that the amount of the catalyst added was changed as indicated in Table 5 and the amount of the carbon dioxide was changed to 0.02 mol. The results of the reaction were as shown in Table 5.

EXAMPLE 49-50

The procedure of EXAMPLE 46 was repeated, except that the amount of the carbon dioxide added was changed to the different amounts indicated in Table 5. The results of the reaction were as shown in Table 5.

EXAMPLES 51-52

The procedure of EXAMPLE 46 was repeated, except that the amount of water as the raw material for the reaction was changed to the varying amounts indicated in Table 5. The results of the reaction were as shown in Table 5.

EXAMPLE 53

The procedure of EXAMPLE 46 was repeated, except that the catalyst was changed to 1.7 g of tungstic acid and the carbon dioxide gas was changed to potassium bicarbonate. The results of the reaction were as shown in Table 5.

EXAMPLE 54

The procedure of EXAMPLE 46 was repeated, except that the propylene oxide as the raw material for the reaction was changed to 43.3 g of 1,2-butylene oxide and the reaction time was changed to 240 minutes. The results of the reaction shown in Table 6 indicate that the conversion of 1,2-butylene oxide was substantially 100% and the selectivity of 1,2-butylene oxide to monobutylene glycol was 85.7%.

TABLE 5

| Example | Raw material PO (g) | Water (g) | CO$_2$ (mole) | Catalyst Kind | to PO (wt.%) | Reaction condition Temp. (°C.) | Pressure (kg/cm$^2$G) | Time (min) | Conversion of PO (mol%) | Selectivity MPG (mol%) | DPG (mol%) | TPG,etc. (mol%) |
|---|---|---|---|---|---|---|---|---|---|---|---|---|
| 37 | 34.8 | 21.6 | 0.01 | PM | 5.7 | 140 | 6 | 120 | 100 | 90.6 | 8.8 | 0.6 |
| 38 | 34.8 | 21.6 | 0.01 | SM | 5.7 | 140 | 6 | 120 | 100 | 90.5 | 8.8 | 0.7 |
| 39 | 34.8 | 21.6 | 0.02 | PM | 10.0 | 140 | 6 | 120 | 100 | 93.1 | 6.7 | 0.2 |
| 40 | 34.8 | 21.6 | 0.001 | PM | 5.7 | 140 | 6 | 120 | 100 | 88.2 | 11.1 | 0.7 |
| 41 | 34.8 | 21.6 | 0.08 | PM | 5.7 | 140 | 6 | 120 | 100 | 86.8 | 12.5 | 0.7 |
| 42 | 34.8 | 31.6 | 0.01 | PM | 5.7 | 140 | 6 | 120 | 100 | 92.8 | 6.8 | 0.4 |
| 43 | 34.8 | 54.0 | 0.01 | PM | 5.7 | 140 | 6 | 120 | 100 | 93.3 | 6.5 | 0.2 |
| 44 | 34.8 | 21.6 | KHCO$_3$ 0.01 | MA | 5.0 | 140 | 6 | 120 | 100 | 90.0 | 9.1 | 0.9 |
| 46 | 34.8 | 21.6 | 0.01 | ST | 5.7 | 140 | 6 | 120 | 100 | 80.4 | 18.6 | 1.0 |
| 47 | 34.8 | 21.6 | 0.01 | PT | 5.7 | 140 | 6 | 120 | 100 | 78.1 | 20.6 | 1.3 |
| 48 | 34.8 | 21.6 | 0.02 | ST | 10.0 | 140 | 6 | 120 | 100 | 85.4 | 13.8 | 0.8 |
| 49 | 34.8 | 21.6 | 0.001 | ST | 5.7 | 140 | 6 | 120 | 100 | 79.5 | 19.3 | 1.2 |
| 50 | 34.8 | 21.6 | 0.08 | ST | 5.7 | 140 | 6 | 120 | 100 | 78.2 | 20.5 | 1.3 |
| 51 | 34.8 | 32.4 | 0.01 | ST | 5.7 | 140 | 6 | 120 | 100 | 85.9 | 13.4 | 0.7 |
| 52 | 34.8 | 54.0 | 0.01 | ST | 5.7 | 140 | 6 | 120 | 100 | 90.1 | 9.2 | 0.7 |
| 53 | 34.8 | 21.6 | KHCO$_3$ 0.01 | TA | 5.0 | 140 | 6 | 120 | 100 | 76.0 | 22.1 | 1.9 |
| Control 5 | 34.8 | 21.6 | 0.01 | — | — | 140 | 6 | 240 | 82.5 | 47.5 | 26.5 | 26.0 |

PO: propylene oxide, MPG: monopropylene glycol, DPG: dipropylene glycol, TPG: tripropylene glycol. Other symbols are the same as in Table 4.

TABLE 6

| | Raw material | | | Catalyst | | Reaction conditions | | | Conversion | Selectivity | |
|---|---|---|---|---|---|---|---|---|---|---|---|
| Example | BO (g) | Water (g) | $CO_2$ (mole) | Kind | to BO (wt.%) | Temp. (°C.) | Pressure ($kg/cm^2 G$) | Time (min.) | of BO (mol%) | MBG (mol%) | Others (mol%) |
| 45 | 43.2 | 21.6 | 0.01 | PM | 5.7 | 140 | 6 | 240 | 100 | 93.7 | 6.3 |
| 54 | 43.3 | 21.6 | 0.01 | ST | 5.7 | 140 | 6 | 240 | 100 | 85.7 | 14.3 |

BO: 1,2-butylene oxide, MBG: mono-1,2-butylene glycol. Other symbols are the same as in Table 4.

EXAMPLE 55

A stainless steel autoclave having an inner volume of 200 ml and equipped with a stirrer was charged with 1.0 g of potassium molybdate, 108.0 g of water and 17.4 g of propylene oxide and then sealed. Then, the inner pressure of the autoclave was raised to 6 kg/$cm^2$ G by introduction of nitrogen gas. The autoclave was submerged in an oil bath kept at 140° C. and left to stand therein for 90 minutes to allow the contents to react. In the course of the reaction, the inner pressure of the autoclave rose to 12.2 kg/$cm^2$ G after 25 minutes of the standing, then fell to 10.1 kg/$cm^2$ G after 45 minutes of the standing and, thereafter, remained substantially unchanged for the remaining period of the reaction time.

The autoclave was cooled in an ice bath and the reaction solution was removed. On analysis, this reaction solution was found to contain less than 0.001% by weight of unaltered propylene oxide, indicating that the conversion of the propylene oxide was substantially 100%. The selectivity of the propylene oxide as the raw material to monopropylene glycol, dipropylene glycol and tripropylene glycol and others was found to be 93.3 mol%, 6.4 mol% and 0.3 mol% respectively.

EXAMPLES 56-60

The procedure of EXAMPLE 55 was repeated, except that the catalyst was changed to the catalysts indicated in Table 7. The results of the reaction were as shown in Table 7.

EXAMPLE 61

The procedure of EXAMPLE 55 was repeated, except that the amount of the catalyst added was changed to that indicated in Table 7. The results of the reaction were as shown in Table 7.

EXAMPLE 62

The procedure of EXAMPLE 55 was repeated, except that the nitrogen gas was changed to carbon dioxide gas as the ambient gas of the reactants. The results of the reaction were as shown in Table 7.

EXAMPLE 63

The procedure of EXAMPLE 55 was repeated, except that the amount of water added was changed to that shown in Table 7. The results of the reaction were as shown in Table 7.

EXAMPLE 64

The procedure of EXAMPLE 55 was repeated, except that 1.0 g of sodium tungstate was used in the place of potassium molybdate. In the course of the reaction, the inner pressure of the autoclave rose to 12.3 kg/$cm^2$ G after 26 minutes of the standing, then fell to 10.1 kg/$cm^2$ G after 45 minutes of the standing and, thereafter, remained substantially unchanged for the remaining period of the reaction time.

The autoclave was cooled in an ice bath and, thereafter, the reaction solution was removed. On analysis, this reaction solution was found to contain less than 0.001% by weight of unaltered propylene oxide, indicating that the conversion of the propylene oxide was substantially 100%. The selectivity of the propylene oxide as the raw material to monopropylene glycol, dipropylene glycol and tripropylene glycol and others was found to be 91.5 mol%, 8.0 mol% and 0.5 mol% respectively.

EXAMPLES 65-69

The procedure of EXAMPLE 64 was repeated, except that the catalyst was changed to the catalysts indicated in Table 7. The results of the reaction were as shown in Table 7.

EXAMPLE 70

The procedure of EXAMPLE 64 was repeated, except that the amount of the catalyst added was changed to the amount indicated in Table 7. The results of the reaction were as shown in Table 7.

EXAMPLE 71

The procedure of EXAMPLE 64 was repeated, except that the nitrogen gas was changed to carbon dioxide gas as the ambient gas of the reactants. The results of the reaction were as shown in Table 7.

EXAMPLE 72

The procedure of EXAMPLE 64 was repeated, except that the amount of water added was changed to that indicated in Table 7. The results of the reaction were as shown in Table 7.

TABLE 7

| | Raw material | | | Catalyst | | Reaction condition | | | conversion | Selectivity | | |
|---|---|---|---|---|---|---|---|---|---|---|---|---|
| Example | PO (g) | Water (g) | Reaction atmosphere | Kind | Amount (g) | Temp. (°C.) | Pressure ($kg/cm^2G$) | Time (min) | of PO (mol%) | MPG (mol%) | DPG (mol%) | TPG.etc. (mol%) |
| 55 | 17.4 | 108 | $N_2$ | PM | 1 | 140 | 6 | 90 | 100 | 93.3 | 6.4 | 0.3 |
| 56 | 17.4 | 108 | $N_2$ | SM | 1 | 140 | 6 | 90 | 100 | 93.2 | 6.5 | 0.3 |
| 57 | 17.4 | 108 | $N_2$ | AM | 1 | 140 | 6 | 90 | 100 | 91.4 | 8.1 | 0.5 |
| 58 | 17.4 | 108 | $N_2$ | MA | 1 | 140 | 6 | 90 | 100 | 91.7 | 7.8 | 0.5 |
| 59 | 17.4 | 108 | $N_2$ | $MoO_3$ | 1 | 140 | 6 | 90 | 100 | 91.5 | 8.0 | 0.5 |
| 60 | 17.4 | 108 | $N_2$ | Mo | 1 | 140 | 6 | 90 | 100 | 91.8 | 7.8 | 0.4 |
| 61 | 17.4 | 108 | $N_2$ | PM | 2 | 140 | 6 | 90 | 100 | 95.0 | 4.8 | 0.2 |
| 62 | 17.4 | 108 | $CO_2$ | PM | 1 | 140 | 6 | 90 | 100 | 93.5 | 6.2 | 0.3 |
| 63 | 17.4 | 54 | $N_2$ | PM | 1 | 140 | 6 | 90 | 100 | 90.1 | 9.1 | 0.8 |
| 64 | 17.4 | 108 | $N_2$ | ST | 1 | 140 | 6 | 90 | 100 | 91.5 | 8.0 | 0.5 |
| 65 | 17.4 | 108 | $N_2$ | PT | 1 | 140 | 6 | 90 | 100 | 91.1 | 8.3 | 0.6 |

TABLE 7-continued

| Example | Raw material PO (g) | Water (g) | Reaction atmosphere | Catalyst Kind | Amount (g) | Reaction condition Temp. (°C.) | Pressure (kg/cm²G) | Time (min) | conversion of PO (mol%) | Selectivity MPG (mol%) | DPG (mol%) | TPG.etc. (mol%) |
|---|---|---|---|---|---|---|---|---|---|---|---|---|
| 66 | 17.4 | 108 | $N_2$ | AT | 1 | 140 | 6 | 90 | 100 | 90.5 | 8.7 | 0.8 |
| 67 | 17.4 | 108 | $N_2$ | WA | 1 | 140 | 6 | 90 | 100 | 90.1 | 9.0 | 0.9 |
| 68 | 17.4 | 108 | $N_2$ | $WO_3$ | 1 | 140 | 6 | 90 | 100 | 90.3 | 8.9 | 0.8 |
| 69 | 17.4 | 108 | $N_2$ | W | 1 | 140 | 6 | 90 | 100 | 90.0 | 9.1 | 0.9 |
| 70 | 17.4 | 108 | $N_2$ | ST | 2 | 140 | 6 | 90 | 100 | 91.7 | 6.9 | 0.4 |
| 71 | 17.4 | 108 | $CO_2$ | ST | 1 | 140 | 6 | 90 | 100 | 91.6 | 7.9 | 0.5 |
| 72 | 17.4 | 54 | $N_2$ | ST | 1 | 140 | 6 | 90 | 100 | 90.5 | 8.7 | 0.8 |

AM: ammonium molybdate, AT: Ammonium tungstate, Other symbols are the same as in Table 4-5.

EXAMPLE 73

A solution was prepared of 1.6 g of potassium molybdate and 14.9 g of water. The solution had a pH value of 10.50. This solution was adjusted to pH 6.35 by addition of molybdic acid as a pH adjusting agent. A stainless steel autoclave having an inner volume of 200 ml and equipped with a stirrer was charged with the solution and 33.0 g of ethylene oxide. It was sealed after nitrogen was introduced therein until the total inner pressure rose to 6 kg/cm²G. The autoclave was then submerged in an oil bath kept at 140° C. and left to stand therein for 90 minutes to allow the contents to react. In the course of the reaction, the inner pressure of the autoclave rose to 21.3 kg/cm² G after 50 minutes of the standing, then fell to 7.7 kg/cm² G after 80 minutes of the standing and, thereafter, remained substantially unchanged for the remaining period of the reaction time. The autoclave was cooled in an ice bath and, thereafter, the reaction solution was removed. On analysis, this reaction solution was found to contain less than 0.01% by weight of unaltered ethylene oxide, indicating that the conversion of the ethylene oxide was substantially 100%.

The selectivity of the ethylene oxide as the raw material to monoethylene glycol, diethylene glycol and triethylene glycol and others was found to be 69.3 mol%, 26.7 mol% and 4.0 mol% respectively.

EXAMPLE 74

The procedure of EXAMPLE 73 was repeated, except that the pH value of the reactant solution was adjusted to 7.0 by using molybdic acid as the pH adjusting agent and the reaction time was changed to 60 minutes. The results of the reaction were as shown in Table 8.

EXAMPLE 75

The procedure of EXAMPLE 73 was repeated, except that the reactant solution was adjusted to pH 8.25 by using potassium bicarbonate as the pH adjusting agent and the reaction time was changed to 60 minutes. The results of the reaction were as shown in Table 8.

EXAMPLE 76

A solution was prepared of 1.6 g of potassium molybdate and 14.9 g of water. This solution had a pH value of 10.50. The solution was adjusted to pH 7.0 by using molybdic acid as a pH adjusting agent. A stainless steel autoclave having an inner volume of 200 ml and equipped with a stirrer was charged with the solution and then sealed. The interior atmosphere of the autoclave was throughly displaced with nitrogen gas. Then, carbon dioxide was introduced into the autoclave until the inner pressure thereof rose to 0.6 kg/cm² G, 33.0 g of ethylene oxide was added thereto and nitrogen gas was introduced therein until the total inner pressure rose to 6 kg/cm² G. The autoclave was submerged in an oil bath kept at 140° C. and left to stand therein for 60 minutes to allow the contents to react. In the course of the reaction, the inner pressure of the autoclave rose to 22.0 kg/cm² G after 25 minutes of the standing, then fell to 7.2 kg/cm² G after 35 minutes of the standing and, thereafter, remained substantially unchanged for the remaining period of the reaction time. The autoclave was cooled in an ice bath and, thereafter, the reaction solution was removed. On analysis, this reaction solution was found to contain less than 0.01% by weight of unaltered ethylene oxide, indicating that the conversion of the ethylene oxide was substantially 100%.

The selectivity of the ethylene oxide as the raw material to monoethylene glycol, diethylene glycol and triethylene glycol and others was found to be 85.8 mol%, 13.7 mol% and 0.5 mol% respectively.

EXAMPLE 77

The procedure of EXAMPLE 76 was repeated, except that the reactant solution was adjusted to pH 8.60 by using potassium bicarbonate as a pH adjusting agent. The results of the reaction were as shown in Table 8.

EXAMPLE 78

A solution was prepared of 1.6 g of molybdic acid and 14.9 g of water. This solution and a pH value of 3.35. The solution was adjusted to pH 7.0 by using potassium hydroxide as a pH adjusting agent. A stainless steel autoclave having an inner volume of 200 ml and equipped with a stirrer was charged with this solution and sealed. The inner atmosphere of the autoclave was throughly displaced with nitrogen gas. Then carbon dioxide gas was introduced therein until the inner pressure of the autoclave rose 1.3 kg/cm² G, 33.0 g of ethylene oxide was added thereto and nitrogen gas was introduced therein until the total inner pressure rose to 6 kg/cm² G. The autoclave was submerged in an oil bath kept at 140° C. and then left to stand therein for 60 minutes to allow the contents to react. In the course of the reaction, the inner pressure of the autoclave rose to 22.0 kg/cm² G after 23 minutes of the standing, then fell to 7.2 kg/cm² G after 45 minutes of the standing and, thereafter, remained substantially unchanged for the remaining period of the reaction time. The autoclave was cooled in an ice bath and, thereafter, the reaction solution was removed. On analysis, this reaction solution was found to contain less than 0.01% by weight of unaltered ethylene oxide, indicating that the conversion of the ethylene oxide was substantially 100%.

The selectivity of the ethylene oxide as the raw material to monoethylene glycol, diethylene glycol and triethylene glycol and others was as shown in Table 8.

EXAMPLE 79

A solution was prepared of 2.0 g of tungstic acid and 21.6 g of water. This solution had a pH value of 4.0. This solution was adjusted to pH 7.0 by using sodium hydroxide as a pH adjusting agent. A stainless steel autoclave having an inner volume of 200 ml and equipped with a stirrer was charged with this solution and sealed. The inner atmosphere of the autoclave was thoroughly displaced with nitrogen gas. Then, carbon dioxide gas was introduced to an inner pressure of 1.7 kg/cm$^2$ G, 34.8 g of propylene oxide was added thereto and nitrogen gas was introduced until the total inner pressure rose to 6 kg/cm$^2$ G. The autoclave was submerged in an oil bath kept at 140° C. and then left to stand therein for 120 minutes. In the course of the reaction, the inner pressure of the autoclave rose to 16.5 kg/cm$^2$ G after 45 minutes of the standing, then fell to 8.2 kg/cm$^2$ G after 100 minutes of the standing and, thereafter, remained substantially unchanged for the remaining period of the reaction time. The autoclave was cooled in an ice bath and, thereafter, the reaction solution was removed. On analysis, the solution was found to contain less than 0.01% by weight of propylene oxide, indicating that the conversion of the propylene oxide was substantially 100%.

The selectivity of the propylene oxide as the raw material to monopropylene glycol, dipropylene glycol and tripropylene glycol and others was found to be as shown in Table 9.

TABLE 8

| Ex-am-ple | Raw material | | Reaction atmos-phere | Catalyst | | Reaction solution pH adjusting agent | pH | Temp. (°C.) | Pres-sure (kg/cm$^2$G) | Time (mm) | Con-version of EO (mol%) | Selectivity | | |
|---|---|---|---|---|---|---|---|---|---|---|---|---|---|---|
| | EO (g) | Water (g) | | Kind | to EO (wt. %) | | | | | | | MEG (mol%) | DEG (mol%) | TEG. etc. (mol%) |
| 73 | 33.0 | 14.9 | N$_2$ | PM | 4.8 | MA | 6.35 | 140 | 6 | 90 | 100 | 69.3 | 26.7 | 4.0 |
| 74 | 33.0 | 14.9 | N$_2$ | PM | 4.8 | MA | 7.00 | 140 | 6 | 60 | 100 | 82.1 | 17.0 | 0.9 |
| 75 | 33.0 | 14.9 | N$_2$ | PM | 4.8 | KHCO$_3$ | 8.25 | 140 | 6 | 60 | 100 | 67.7 | 26.9 | 5.4 |
| 76 | 33.0 | 14.9 | CO$_2$ 0.005 mole | PM | 4.8 | PM | 7.00 | 140 | 6 | 60 | 100 | 85.8 | 13.7 | 0.5 |
| 77 | 33.0 | 14.9 | CO$_2$ 0.005 mole | PM | 4.8 | KHCO$_3$ | 8.60 | 140 | 6 | 60 | 100 | 83.9 | 15.6 | 0.5 |
| 78 | 33.0 | 14.9 | 0.01 mole | MA | 4.8 | KOH | 7.00 | 140 | 6 | 60 | 100 | 86.2 | 13.4 | 0.4 |

TABLE 9

| Ex-am-ple | Raw material | | Reaction atmos-phere | Catalyst | | Reaction solution pH adjusting agent | pH | Temp. (°C.) | Pres-sure (kg/cm$^2$G) | Time (min.) | Con-version of PO (mol%) | Selectivity | | |
|---|---|---|---|---|---|---|---|---|---|---|---|---|---|---|
| | PO (g) | Water (g) | | Kind | To PO (wt.%) | | | | | | | MPG (mol%) | DPG (mol%) | TPG, etc. (mol%) |
| 79 | 34.8 | 21.6 | CO$_2$ 0.01 mole | TA | 5.7 | NaOH | 7.0 | 140 | 6 | 120 | 100 | 82.3 | 16.9 | 0.8 |

What is claimed is:

1. A process for the production of substituted or unsubstituted ethylene glycols, which comprises causing a corresponding ethylene oxide of the formula

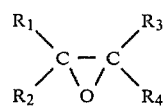

wherein R$_1$, R$_2$, R$_3$, and R$_4$ each denote a hydrogen atom, an alkyl group having 1 to 3 carbon atoms, an aryl group having 6 carbon atoms, an alkenyl group having 2 or 3 carbon atoms or a cycloalkyl group having 3 to 6 carbon atoms to react with water in the presence of a catalyst of at least one member selected from the group consisting of metallic molybdenum, metallic tungsten, molybdenum compounds and tungstic acid and the salts thereof in an atmosphere of nitrogen or carbon dioxide.

2. A process according to claim 1, wherein the amount of the catalyst is not less than 0.01% by weight based on the ethylene oxide.

3. A process according to claim 2, wherein the amount of the catalyst is in the range of from 0.1 to 100% by weight based on the ethylene oxide.

4. A process according to claim 3, wherein the amount of the catalyst is in the range of from 1 to 20% by weight based on the ethylene oxide.

5. A process according to claim 1, wherein the reaction is carried out at a temperature in the range of from 20° to 250° C.

6. A process according to claim 5, wherein the reaction is carried out at a temperature in the range of from 50° to 200° C.

7. A process according to claim 1, wherein the alkylene oxide is one member selected from the group consisting of ethylene oxides having 2 to 4 carbon atoms.

8. A process according to claim 1, therein the catalyst is metallic molybdenum.

9. A process according to claim 1, wherein the catalyst is a molybdenum compound.

10. A process according to claim 9, wherein the molybdenum compound is molybdic acid or a salt thereof.

11. A process according to claim 10, wherein the salt of molybdic acid is an alkali metal salt.

12. A process according to claim 1, wherein the catalyst is metallic tungsten.

13. A process according to claim 7 wherein the ethylene oxide is ethylene oxide or propylene oxide.

14. A process according to claim 1, wherein the catalyst is tungstic acid or a salt thereof.

15. A process according to claim 14, wherein the salt of tungstic acid is an alkali metal salt.

16. A process according to claim 1, wherein the amount of water is 1 to 30 mols per mol of the ethylene oxide.

17. A process according to claim 16, wherein the amount of water is 1 to 20 mols per mol of the ethylene oxide.

18. A process according to claim 1, wherein the reaction is carried out in the presence of carbon dioxide.

19. A process according to claim 18, wherein the amount of carbon dioxide is 0.00001 to 1 mol per mol of the ethylene oxide.

20. A process according to claim 19, wherein the amount of carbon dioxide is 0.001 to 1 mol per mol of the ethylene oxide.

21. A process according to claim 18, wherein the amount of water is 1.01 to 5 mols per mol of the ethylene oxide.

22. A process according to claim 1, wherein the reactant solution has a pH value in the range of from 5 to 10.

23. A process according to claim 22, wherein the amount of water is 1.01 to 5 mols per mol of the alkylene oxide.

* * * * *